United States Patent
Dulaff

(10) Patent No.: US 9,616,426 B2
(45) Date of Patent: Apr. 11, 2017

(54) PIPETTOR, REAGENT, AND WASH SOLUTION HEATER

(71) Applicant: Siemens Healthcare Diagnostics Inc., Tarrytown, NY (US)

(72) Inventor: Paul Dulaff, Columbia, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/423,412

(22) PCT Filed: Aug. 23, 2013

(86) PCT No.: PCT/US2013/056319
§ 371 (c)(1),
(2) Date: Feb. 23, 2015

(87) PCT Pub. No.: WO2014/035804
PCT Pub. Date: Mar. 6, 2014

(65) Prior Publication Data
US 2015/0224503 A1    Aug. 13, 2015

Related U.S. Application Data

(60) Provisional application No. 61/694,324, filed on Aug. 29, 2012.

(51) Int. Cl.
*H05B 6/10* (2006.01)
*B01L 7/00* (2006.01)
(Continued)

(52) U.S. Cl.
CPC ............. *B01L 7/00* (2013.01); *G01N 1/44* (2013.01); *G01N 35/1004* (2013.01);
(Continued)

(58) Field of Classification Search
CPC ... H05B 6/108; B01L 7/00; B01L 7/52; B01L 2300/0627; B01L 3/50851;
(Continued)

(56) References Cited

U.S. PATENT DOCUMENTS 3,737,627 A    6/1973  Williard et al.
4,560,849 A   12/1985  Migliori et al.
(Continued)

FOREIGN PATENT DOCUMENTS

DE         41 02 336 A1      8/1992
DE      20 2009 009371 U1    9/2009
(Continued)

OTHER PUBLICATIONS

PCT International Search Report and Written Opinion dated Jan. 24, 2014 (13 Pages).
Extended EP Search Report dated May 2, 2016 of corresponding European Application No. 13833248.1.

*Primary Examiner* — Hung D Nguyen

(57) ABSTRACT

A heater for heating fluidic elements and fluids is provided. The heater quickly and efficiently heats elements and samples without occupying a lot of space in in vitro diagnostic environments. The heater includes an induction coil, sized and configured to allow for a fluidic element to be placed therein, and induction circuitry coupled to the induction coil that facilitates induction heating through electromagnetic induction. A current is generated to pass through the induction coil, creating a field within the induction coil that generates heat that is transferrable to conductive objects placed within the field. In this manner, heat is transferred to the fluidic element and to fluids in contact with the fluidic element.

15 Claims, 6 Drawing Sheets

(51) Int. Cl.
*G01N 1/44* (2006.01)
*G01N 35/10* (2006.01)
*B01L 3/02* (2006.01)
*G01N 35/00* (2006.01)

(52) U.S. Cl.
CPC ............ *H05B 6/108* (2013.01); *B01L 3/0275* (2013.01); *B01L 2200/147* (2013.01); *B01L 2300/0627* (2013.01); *B01L 2300/1816* (2013.01); *G01N 2035/00425* (2013.01); *G01N 2035/1048* (2013.01)

(58) Field of Classification Search
CPC ............ B01L 3/0275; B01L 2200/147; B01L 2300/1816; G01N 1/44; G01N 35/1004; G01N 2035/1048; G01N 2035/00425
USPC ....... 219/628, 629, 630, 672, 674, 665, 663, 219/649, 650, 653, 635; 73/863.11, 73/863.12, 864.24, 864.25
See application file for complete search history.

(56) References Cited

U.S. PATENT DOCUMENTS

| | | | |
|---|---|---|---|
| 5,178,019 A | 1/1993 | Keiter | |
| 5,287,758 A | 2/1994 | Geiss et al. | |
| 6,021,253 A | 2/2000 | Bell | |
| 6,633,785 B1* | 10/2003 | Kasahara | B01L 7/52 435/286.1 |
| 6,930,292 B1 | 8/2005 | Winther et al. | |
| 2004/0265173 A1 | 12/2004 | Matsumoto et al. | |
| 2007/0026442 A1* | 2/2007 | Calasso | G01N 33/54313 435/6.12 |

FOREIGN PATENT DOCUMENTS

| | | |
|---|---|---|
| EP | 0 546 463 A1 | 6/1993 |
| EP | 0546463 A1 | 9/1993 |
| JP | 3 110056 B2 | 11/2000 |
| JP | 3110056 B2 * | 11/2000 |

* cited by examiner

PIPETTOR, REAGENT, AND WASH SOLUTION HEATER

TECHNOLOGY FIELD

The present invention relates generally to heating fluidic elements and fluids for use in analysis environments, and more particularly to utilizing induction coils for heating fluidic elements and fluids.

BACKGROUND

Fluidic elements, including fluid handling elements such as pipettors and probes, are used in analysis environments such as an in vitro diagnostics (IVD) environments in which fluids, such as human samples and reagents, are used in various tests. For example, a human sample may be disposed in a tube which is disposed on a carousel or other conveying mechanism to convey the tube through various stations, such as a pipetting station for a pipettor to aspirate a sample of the fluid. The pipettor is lowered into the tube for the aspiration of the sample and may then be dispensed into another unit to be mixed or combined with a reagent, for example. Depending on the test or tests to be performed on the sample, there may be a need to heat the pipettor and/or the sample fluid contained therein. Moreover, the pipettor may be used for many different fluids, resulting in a need to thoroughly clean the pipettor between uses, reducing or eliminating carry-over between the fluids.

This document describes an exemplary heater that can be utilized in IVD environments to quickly and efficiently heat fluidic elements and fluids, as well as clean fluidic elements.

SUMMARY

Embodiments of the present invention provide a heater for heating fluidic elements and fluids. The heater includes an induction coil sized and configured to allow for a fluidic element to be placed therein; and induction circuitry coupled to the induction coil and configured to generate a current to pass through the induction coil, thereby creating a field within the induction coil that generates heat transferrable to the fluidic element placed therein. In an embodiment, the current generated to pass through the induction coil comprises a radio-frequency alternating current, and the field created comprises a radio-frequency magnetic field.

According to an embodiment, a sensor may be integrated with the heater, the sensor being configured to detect a temperature of the fluidic element placed within the induction coil.

According to an embodiment, the heater may also include level-sensing circuitry configured to impose a signal on the fluidic element and detect a change in the imposed signal, the change in the imposed signal indicating that the fluidic element is in contact with a fluid.

Other embodiments of the present invention are directed to a system for use in an in vitro diagnostics (IVD) environment for heating fluidic elements and fluids. The system includes a sample tube configured to contain therein a fluid; a fluidic element configured to aspirate a sample fluid from the fluid contained within the sample tube; and a heater. The heater includes an induction coil sized and configured to allow for the fluidic element to be placed therein; and induction circuitry coupled to the induction coil and configured to generate a current to pass through the induction coil, thereby creating a field within the induction coil that generates heat transferrable to the fluidic element placed therein. Heat is imparted to the sample fluid from the heat transferred to the fluidic element.

According to an embodiment, the heat is transferred to the fluidic element at one or more of: (i) prior to aspiration of the sample fluid; (ii) during aspiration of the sample fluid; and (iii) after aspiration of the sample fluid.

The system, according to an embodiment, includes a sensor configured to detect a temperature of the fluidic element placed within the induction coil. The sensor is coupled to at least one of the fluidic element and the heater.

In another embodiment, a sensor is coupled to a dispensing unit, where the sensor is configured to detect a temperature of a portion of the sample fluid dispensed from the fluidic element to the dispensing unit.

The system may also include a washing unit configured to wash the fluidic element after dispensing the sample fluid, wherein the heater generates a high temperature heat transferrable to the fluidic element placed within the induction coil to eliminate carryover on the fluidic element.

In some embodiments, the fluidic element is configured to move between the sample tube and the heater. In other embodiments, the heater is attached to the fluidic element.

The system may also include, according to an embodiment, level-sensing circuitry configured to impose a signal on the fluidic element and detect a change in the imposed signal. The change in the imposed signal serves as an indication that the fluidic element is in contact with the fluid contained within the sample tube.

Other embodiments are related to a method of heating fluidic elements and fluids. The method includes providing a fluidic element for insertion into an induction coil of a heater; applying, through induction circuitry coupled to the heater, a current to pass through the induction coil, thereby creating a field within the induction coil that generates heat transferrable to the fluidic element placed therein; and aspirating, by the fluidic element, a sample fluid from a sample tube configured to contain therein a fluid, wherein heat is imparted to the sample fluid from the heat transferred to the fluidic element.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Embodiments of the present invention relate to a heater for heating fluidic elements and fluids. Embodiments of the present invention are particularly well suited for, but in no way limited to, an in vitro diagnostics (IVD) environment in which fluidic elements are used for various testing and analyses of fluids. An analyzer, such as an automatic analyzer, may be used for the testing and analyses. The fluidic elements may include, but are in no way limited to, fluid handling elements such as probes and pipettors that are configured to draw up and release fluids (i.e., aspirate). Reference herein to fluids includes, but is no way limited to, human samples or specimens, reagents, and combinations thereof. Fluids may also include wash solutions.

In IVD environments, there is often a need to heat a human sample or a reagent; for example, for a particular reaction to occur a sample may be required to be at a certain temperature above room temperature. As automatic analyzers handle multitudes of samples, there is a need for high throughput; thus there is a need to provide a heating device that quickly and efficiently heats samples without occupying a lot of space on the automatic analyzer. The present invention fulfills these needs.

Figure 1B:
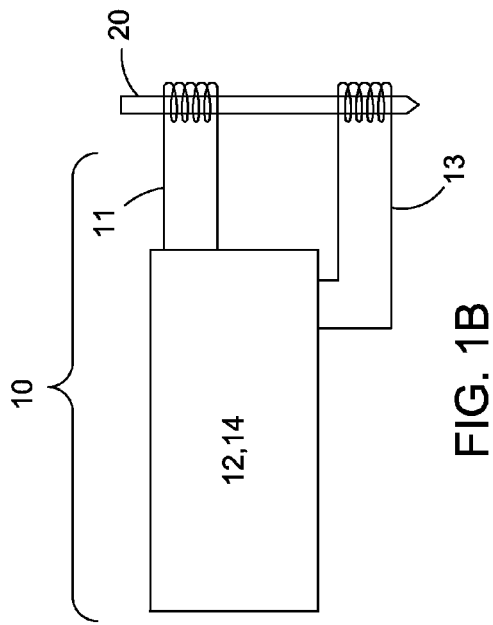
FIGS. 1A, 1B, and 1C illustrate an exemplary heater and use thereof, according to an embodiment.
Figure 1C:
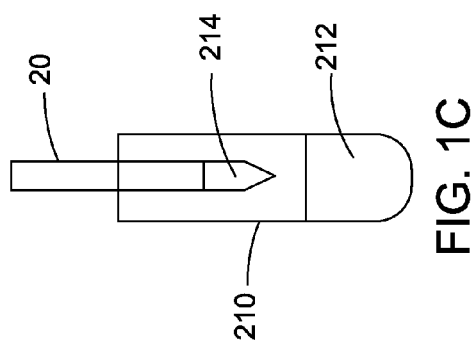
Figure 1A:
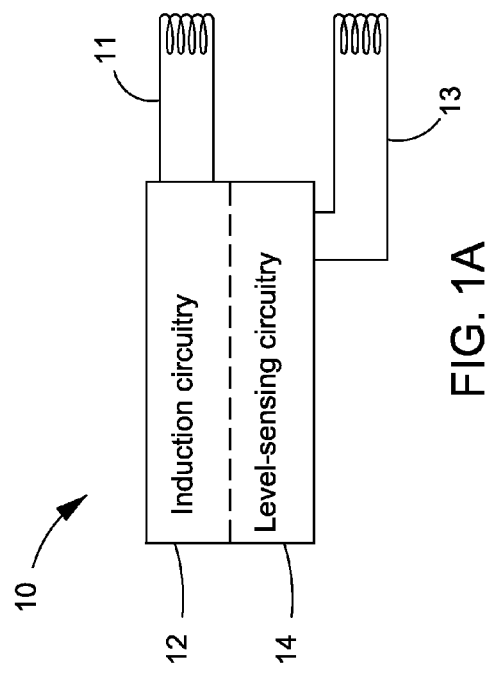

FIGS. 1A and 1B depict an exemplary heater 10 according to an embodiment. The heater 10 includes an induction coil 11 and induction circuitry 12. The induction coil 11 is sized and configured to allow for a fluidic element 20 to be placed therein, as shown in FIG. 1B. The induction coil 11 may be sized so that various fluidic elements of varying sizes are able to be placed within the induction coil 11.

The induction circuitry 12 facilitates induction heating through electromagnetic induction. The induction circuitry 12 is coupled to the induction coil 11 and is configured to generate a current to pass through the induction coil 11. The current creates a field within the induction coil 11 that generates heat that is transferrable to conductive objects placed within the field. In this manner, heat is transferred to the fluidic element 20 placed within the induction coil 11. In some embodiments, the current generated to pass through the induction coil 11 a radio-frequency alternating current, and the field created is a radio-frequency magnetic field.

FIG. 1C illustrates the fluidic element 20 being utilized according to an embodiment of the present invention. The fluidic element 20 aspirates a sample fluid 214 from a fluid 212 in a sample tube 210. In some embodiments, the fluidic element 20 is a pipettor and the sample fluid 214 is a human sample. As the heat created from the field within the induction coil 11 is transferred to the fluidic element 20, the heat is imparted on the sample fluid 214 contained within the fluidic element 20.

As the induction coil 11 surrounds a portion of the fluidic element 20, the heater 10 may provide for selective heating of portions of the fluidic element 20 (i.e., the portions adjacent to or in proximity of the induction coil). The selective heating may be advantageous when aspirating a sample fluid 214, for example, as it may be undesirable for the entire fluid 212 in the sample tube 210 to be heated. As a bottom portion of the fluidic element 20 is not directly heated by the induction coil 11, according to an embodiment, the portion of the fluid 212 in contact with the bottom portion of the fluidic element 20 is also not heated.

In other embodiments, the fluidic element 20 may be inserted into the sample tube 210 to heat the contents contained therein, without removing (i.e., aspirating) a sample portion. The heating, in this embodiment, is achieved through the natural transfer of heat from the fluidic element 20 to the contents of the sample tube 210 (i.e., the fluid 212).

Again referring to FIGS. 1A and 1B, according to an embodiment, the heater 10 may include level-sensing circuitry 14, including a sensing coil 13, configured to impose a signal on the fluidic element 20 and detect a change in the imposed signal. The change in the imposed signal serves as an indication that the fluidic element 20 is in contact with fluid (e.g., the fluid 212 contained within the sample tube 210).

In some embodiments, the heater 10 is a separate component from the fluidic element 20, and the fluidic element 20 is moved to be placed within the induction coil 11 of the heater 10. In other embodiments, the heater 10 is integrated with or otherwise attached to the fluidic element 20.

Figure 2:
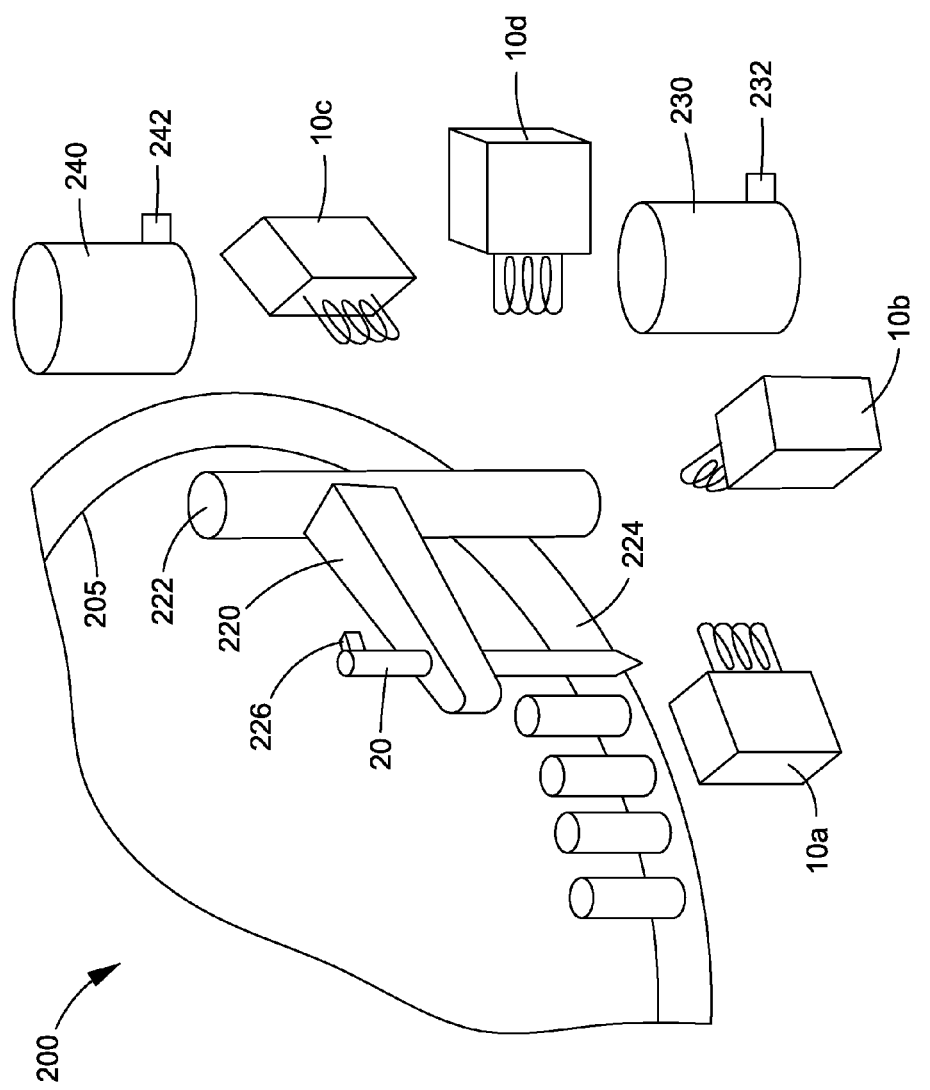
FIG. 2 is an illustration of a portion of a system used with the present invention, according to an embodiment.

FIG. 2 illustrates an exemplary system 200 that may be used with the present invention. The fluidic element 20 is attached to a moveable arm 220, which is secured to a base 222. The moveable arm 220 provides for movement of the element 20 between the various system components as further described below. In some embodiments, the moveable arm 220 may also be extendible to provide for placement at the various system components. In some embodiments, a sensor 226 is positioned on or in proximity to the fluidic element 20 for detecting the temperature of the fluidic element 20. In an embodiment, the sensor 226 may be integrated with the heater 10.

A carousel 205, is provided for holding and conveying sample tubes, such as the sample tube 210 in which the fluid 212 is contained. Other conveying mechanisms may also or additionally be used. The fluidic element 20 aspirates the sample fluid 214 from the fluid 212 in the sample tube 210 at an aspiration point 224. In some embodiments, the fluidic element 20 is a pipettor and the sample fluid is a human sample.

A dispensing unit 230 is provided for receiving the aspirated sample fluid 214 from the fluidic element 20. A sensor 232 may be disposed on or in proximity to the dispensing unit 230 to detect the temperature of the aspirated sample fluid 214 being dispensed in the dispensing unit 230. The dispensing unit 230 may be used for various tests or analyses, for example.

A washing unit 240 is provided to wash the fluidic element 20 after aspiration and dispensing, or after other operations performed by the fluidic element 20. The washing unit 240 may include a washing solution in which the fluidic element 20 is immersed for eliminating remnants of the fluid 212 and the sample fluid 214. The washing unit 240 may include other instruments to assist in the cleaning. A sensor 242 may be disposed on or in proximity to the washing unit 240 to detect the temperature of the washing solution or the fluidic element 20.

At or in proximity to one or more of the system components described above (the aspiration point 224, the dispensing unit 230, and the washing unit 240), a heater 10 (heater 10a at the aspiration point 224, heater 10b at the dispensing unit 230, and heater 10c at the washing unit 240) may be provided for heating the fluidic element 20. One or more additional heaters (such as the heater 10d shown in FIG. 2) may also be disposed at various locations in the system 200. The heaters 10a, 10b, 10c, and 10d allow for heating the fluidic element 20.

At the aspiration point 224, the fluidic element 20 may be heated with the heater 10a; when the sample fluid 214 is aspirated, the sample fluid 214 is also heated as the heat is transferred from the fluidic element 20 to the sample fluid 214 contained therein. The fluidic element 20 may be heated through the induction coil 11 and then removed from the induction coil 11 prior to the aspiration. Alternately, the sample fluid 214 may be aspirated prior to the heating of both the fluidic element 20 and the sample fluid 214. Or, the heating and aspirating may occur at or near the same time;

the fluidic element 20 is inserted into the induction coil 11 and performs the aspiration while contained within the induction coil 11.

The sensor 226 on or near the fluidic element 20 may be used to detect the temperature of the fluidic element 20, which may be used to indicate when the sample fluid 214 reaches the desired temperature.

The level-sensing circuitry 14 may be utilized at the aspiration point to detect when the fluidic element 20 is in contact with the fluid 212 contained within the sample tube 210 by imposing a signal on the fluidic element 20 and detecting a change in the imposed signal. The change in the imposed signal serves as an indication that the fluidic element 20 is in contact with the fluid 212.

At the dispensing unit 230, the fluidic element 20 may be heated with the heater 10b. As the fluidic element 20 contains the sample fluid 214, the sample fluid 214 is also heated as the heat is transferred from the fluidic element 20 to the sample fluid 214 contained therein. The fluidic element 20 may be heated through the induction coil 11 and then removed from the induction coil 11 prior to the dispensing of the sample fluid 214 in the dispensing unit 230.

The sensor 226 on or near the fluidic element 20 or the sensor 232 may be used to detect the temperature of the fluidic element 20 and/or the sample fluid 214. The sensors 226 or 232 may measure the temperature of the fluidic element 20, which may be used to determine if the sample fluid 214 is at a desired temperature. Alternately, the sensor 232 at the dispensing unit 230 may measure the temperature of a small portion of the sample fluid 214 that is dispensed from the fluidic element 20 to determine if the desired temperature is met.

In another embodiment, the fluidic element 20 may be heated by the induction coil 11 and then inserted into the dispensing unit 230 to heat the contents contained therein. The sensor 232 may be used to measure the temperature of the contents.

At the washing unit 240, the fluidic element 20 may be heated with the heater 10c prior to and/or after being washed. The heater 10c may generate a high heat that eliminates any carryover from the fluid 212 and the sample fluid 214.

The sensor 226 on or near the fluidic element 20 or the sensor 242 may be used to detect the temperature of the fluidic element 20 to determine if the fluidic element 20 is at a desired temperature.

The heater 10d may be used instead of or in addition to any of the heaters 10a, 10b, and 10c. As the heater 10d is positioned at a dedicated location, the fluidic element 20 may be moved, via the moveable arm 220, to the heater 10d before aspiration, after aspiration and prior to dispensing, after dispensing, and/or after washing.

In addition to or instead of utilizing the sensors 226, 232, and 242 to detect the temperature of the fluidic element 20 and/or the sample fluid 214, an algorithm may instead be used to determine the temperature. The algorithm may be based on time and power level applied to the induction coil 11 by the induction circuitry 12. Alternatively, an infrared detector may be used to measure the energy emitted from the fluidic element 20.

Figure 3A:
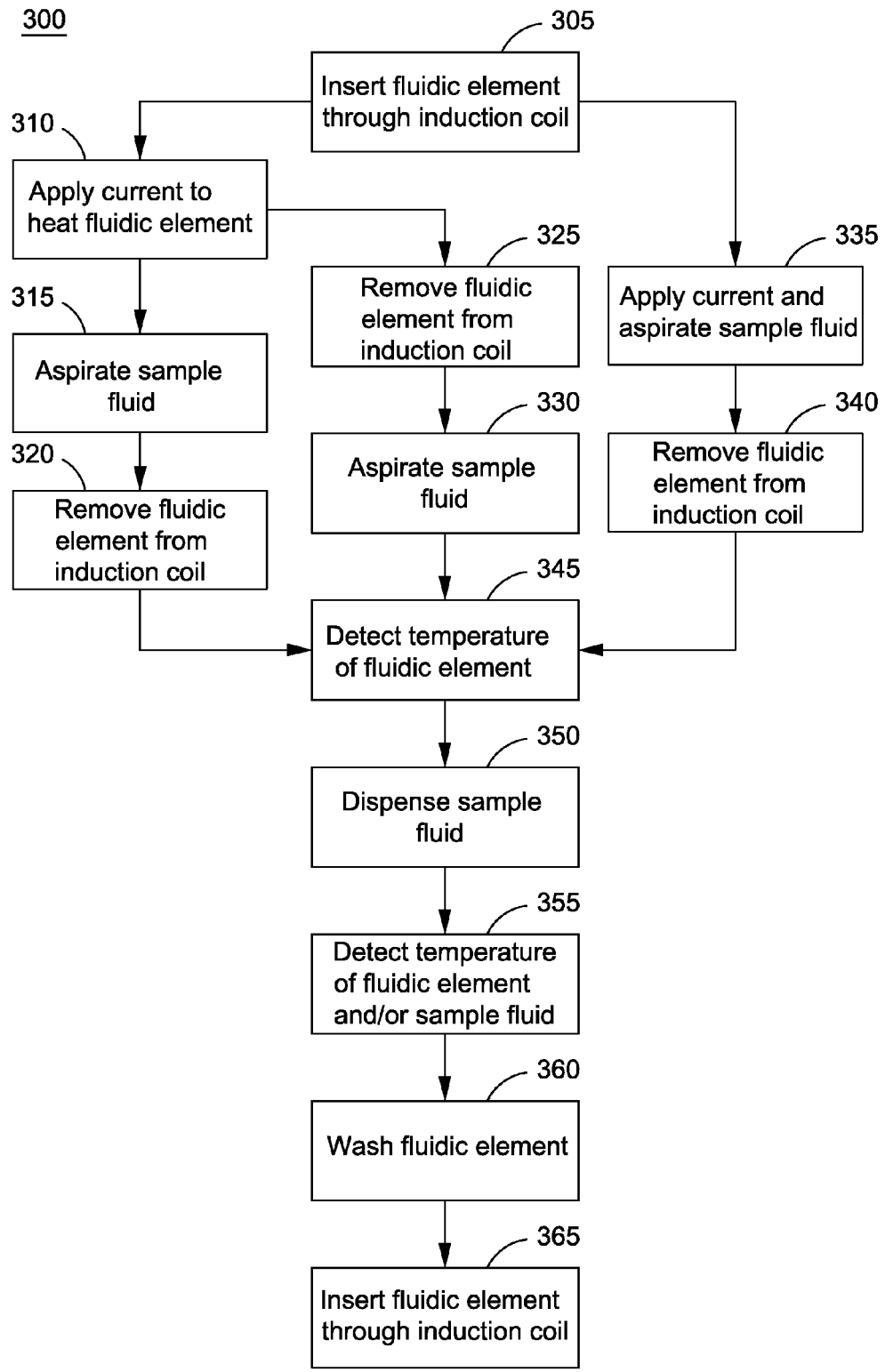
FIGS. 3A and 3B are flowcharts of a method of heating fluidic elements and fluids, according to embodiments.

FIG. 3A is a flowchart 300 illustrating a method of heating fluidic elements and fluids, such as the fluidic element 20 and the fluid 212 contained within the sample tube 210.

At 305, the fluidic element 20 is inserted through the induction coil 11 of the heater 10. This step may not be required if the heater 10 is connected to or integrated with the fluidic element 20.

According to an embodiment, at 310, a current is applied from the induction circuitry 12 to pass through the induction coil 11, thereby creating a field within the induction coil 11 that generates heat transferrable to the fluidic element 20. At 315, a sample fluid 214 is aspirated by the fluidic element 20 from the sample tube 210. The heat transferred to the fluidic element 20 is naturally imparted on the sample fluid 214 contained within the fluidic element 20. At 320, the fluidic element 20 may be removed from the induction coil 11, via, for example the moveable arm 220.

According to another embodiment, at 325, the fluidic element 20 is removed prior to aspiration, via, for example, the moveable arm 220. At 330, a sample fluid 214 is aspirated by the fluidic element 20. In an embodiment in which the heater 10 is connected to or integrated with the fluidic element 20, the fluidic element 20 may not be removed from the induction coil 11.

According to another embodiment, current may be applied to the induction circuitry 12 at the same time or during aspiration. Thus, at 335, a current is applied from the induction circuitry 12 to pass through the induction coil 11 and a sample fluid 214 is aspirated by the fluidic element 20 from the sample tube 210. At 340, the fluidic element 20 may be removed from the induction coil 11, via, for example the moveable arm 220. In an embodiment in which the heater 10 is connected to or integrated with the fluidic element 20, the fluidic element 20 may not be removed from the induction coil 11.

At 345, a sensor, such as the sensor 226, may, according to an embodiment, detect a temperature of the fluidic element 20. This may occur prior to the removal of the fluidic element 20 from the induction coil 11 at 320, 325, or 340.

At 350, the sample fluid 214 is dispensed from the fluidic element 20 into, for example, a dispensing unit 230. At 355, a sensor, such as the sensor 226 or the sensor 232 associated with the dispensing unit 230, may be used to measure the temperature of the fluidic element 20. The sensor 232 may also be used to detect a temperature of a portion of the sample fluid 214 dispensed from the fluidic element 20 to the dispensing unit 230. In this embodiment, the portion may be a small amount of the sample fluid 214 to verify the sample fluid 214 is at a desired or required temperature.

At 360, the fluidic element 20 is washed at the washing unit 240. At 365, to eliminate carryover of fluids on the fluidic element 20, the fluidic element 20 is inserted into the induction coil 11 of the heater 10, such as the heater 10c or 10d. The heat generated by the heater 10 is a high temperature heat that is transferred to the fluidic element 20 when inserted within the induction coil 11.

Figure 3B:
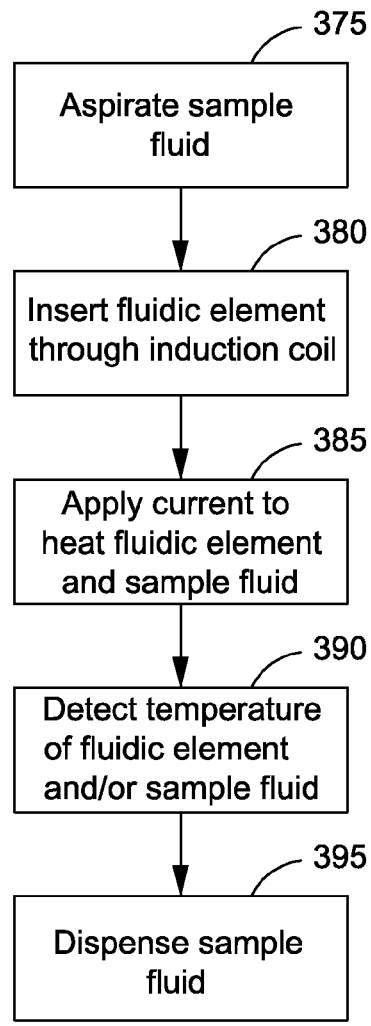

FIG. 3B is a flowchart 370 illustrating another method of heating fluidic elements and fluids, such as the fluidic element 20 and the fluid 212 contained within the sample tube 210.

At 375, a sample fluid 214 is aspirated by the fluidic element 20 from the sample tube 210. The aspiration occurs at the aspiration point 324.

At 380, the fluidic element 20 is inserted through the induction coil 11 of the heater 10, such as the heater 10c at the dispensing unit 230. This step may not be required if the heater 10 is connected to or integrated with the fluidic element 20.

At 385, a current is applied from the induction circuitry 12 to pass through the induction coil 11, thereby creating a field within the induction coil 11 that generates heat transferrable to the fluidic element 20, which is in turn transferred to the sample fluid 214 contained within the fluidic element 20.

At 390, a sensor, such as the sensor 226 or the sensor 232 associated with the dispensing unit 230, may be used to measure the temperature of the fluidic element 20. The sensor 232 may also or alternately be used to detect a temperature of a portion of the sample fluid 214 dispensed from the fluidic element 20 to the dispensing unit 230. In this embodiment, the portion may be a small amount of the sample fluid 214 to verify the sample fluid 214 is at the desired or required temperature.

At 395, the sample fluid 214 is dispensed from the fluidic element 20 into, for example, the dispensing unit 230. The fluidic element 20 may be removed from the induction coil 11 prior to or following the dispensing of the sample fluid 214. In an embodiment in which the heater 10 is connected to or integrated with the fluidic element 20, the fluidic element 20 may not be removed from the induction coil 11.

The washing operations described in relation to FIG. 3A (i.e., 360 and 365) may be performed to eliminate carryover of fluids on the fluidic element 20.

Figure 4:
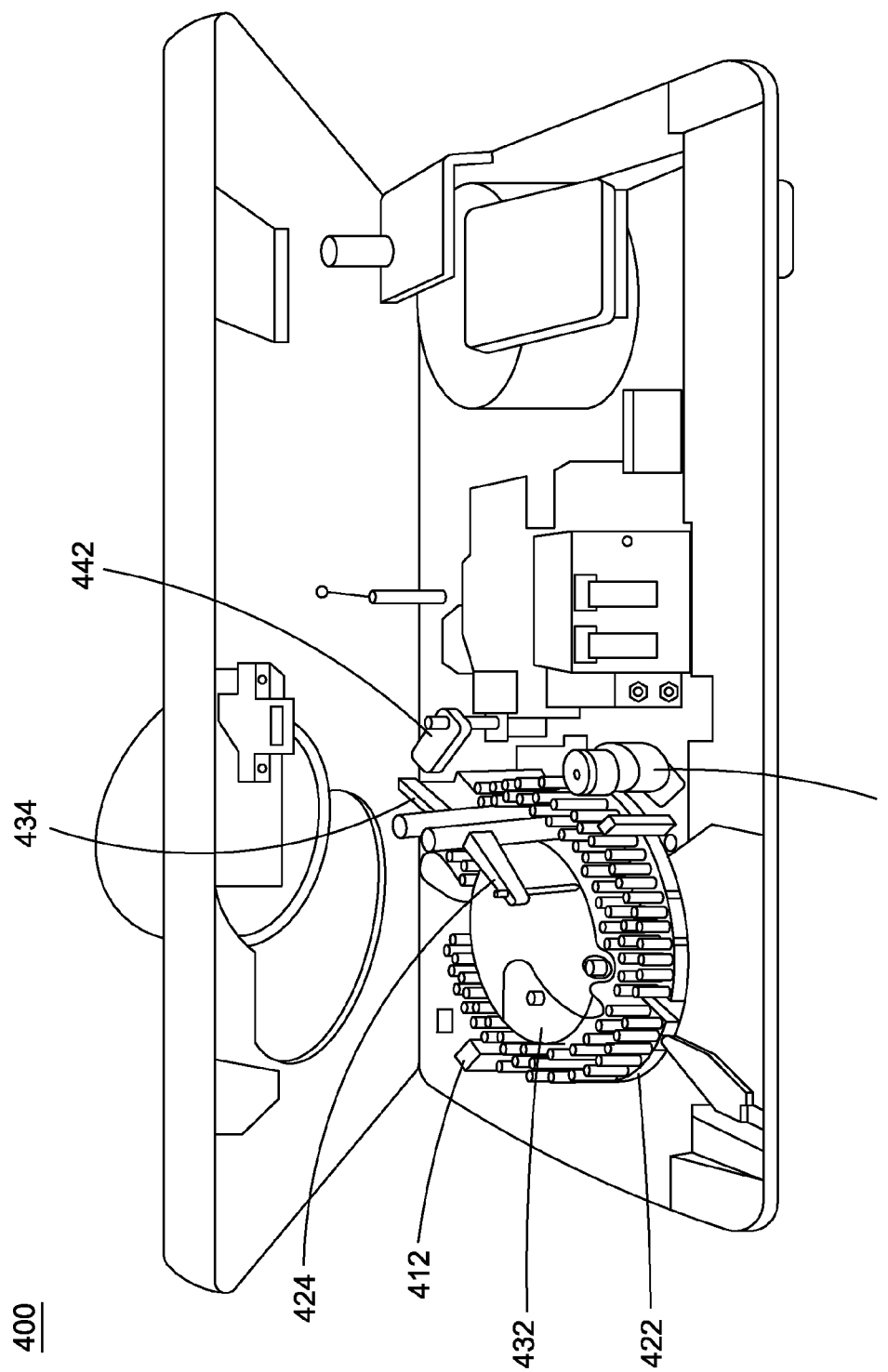
FIG. 4 is a partial view of an automated analyzer that can be used with the present invention, according to an embodiment.

FIG. 4 shows a partial view of an automatic analyzer 400, which is an IMMULITE 2000™ manufactured by Siemens Medical Solutions. The automatic analyzer 400 is merely representative of one automatic analyzer that may be used with the present invention. The present invention may be implemented with other automatic analyzers or other fluid sample devices. The automatic analyzer 400 shown in FIG. 4 is described herein for illustrative purposes to better describe the present invention.

Referring to FIG. 4, sample carrier tubes are transported by a sample carousel 422 to a sample pipettor 424, which may extend from an arm for accessing the sample carrier tube 420. Reagents are transported in the reagent carousel 432 to a reagent pipettor 434, which may also extend from an arm for accessing the reagents. A barcode reader 412 may be included to identify information related to the samples or reagents that are passed through the barcode reader 412. A wash station 442 is provided for washing the sample pipettor 424 and the reagent pipettor 34. The sample pipettor 424 and the reagent pipettor 434 may extend to other carriers or stations, such as a sample dilution well 444.

Figure 5:
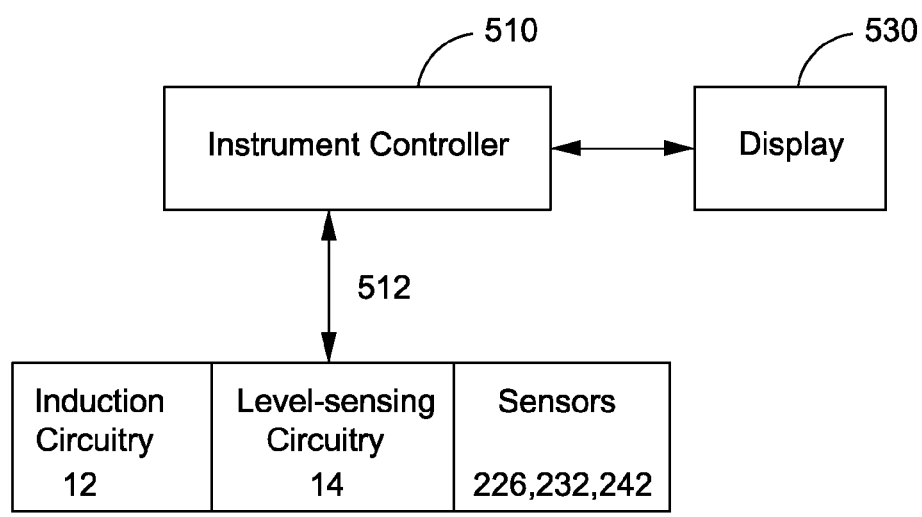
FIG. 5 is a block diagram of a system used with the present invention, according to an embodiment.

FIG. 5 is a block diagram of a system 500 used with the present invention, according to an embodiment. An instrument controller 510 may be a processing device, computing device, processor, or the like for performing calculations and operations described herein. The instrument controller 510 interfaces with the automatic analyzer including the induction circuitry 12 and the level sensing circuitry 14 through data communication lines 512, and may also interface with the various sensors 226, 232, and 242. The instrument controller 520 may also interface with one or more memory devices (not shown) such as read only memory (ROM), random access memory (RAM), and one or more optional non-transitory memory devices such as, for example, an external or internal DVD drive, a CD ROM drive, a hard drive, flash memory, a USB drive, or the like. The memory devices may be configured to include individual files and/or one or more databases for storing any software modules, instructions, or data.

Program instructions, software, or interactive modules for performing any of the functional steps associated with the processes as described above may be stored in the ROM and/or the RAM. Optionally, the program instructions may be stored on a tangible computer readable medium such as a compact disk, a digital disk, flash memory, a memory card, a USB drive, an optical disc storage medium, such as a Blu-Ray™ disc, and/or other recording medium.

An optional display interface may permit information from the instrument controller 510 to be displayed on the display 530 in audio, visual, graphic, and/or alphanumeric format. Communication with external devices may occur using various communication ports that may be attached to one or more communications networks, such as the Internet or a local area network, or directly to a portable computing device such as a notebook computer. An interface may allow for receipt of data from input devices such as a keyboard, a mouse, a joystick, a touch screen, a remote control, a pointing device, a video input device, an audio input device, and the like.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

I claim:

1. A heater for heating fluidic elements and fluids in an in vitro diagnostics (IVD) environment, the heater comprising:
   an induction coil sized and configured to allow for a fluidic element to be placed therein;
   induction circuitry coupled to the induction coil and configured to generate a current to pass through the induction coil, thereby creating a field within the induction coil that generates heat transferrable to the fluidic element placed therein;
   a sensing coil sized and configured to allow for the fluidic element to be placed therein; and
   level-sensing circuitry coupled to the sensing coil and configured to impose a signal on the fluidic element when placed in the sensing coil and detect a change in the imposed signal, wherein the change in the imposed signal serves as an indication that the fluidic element is in contact with a fluid;
   wherein the fluidic element is configured to aspirate a sample fluid from the fluid contained within a sample tube; and
   wherein the heat is transferred to the fluidic element prior to aspiration, during aspiration, and following aspiration depending upon an order in which the fluidic element is placed within the induction coil and aspirates the sample fluid.

2. The heater of claim 1, further comprising:
   a sensor configured to detect a temperature of the fluidic element placed within the induction coil.

3. The heater of claim 1, wherein the current generated to pass through the induction coil comprises a radio-frequency alternating current, and wherein the field created comprises a radio-frequency magnetic field.

4. A system for use in an in vitro diagnostics (IVD) environment for heating fluidic elements and fluids, the system comprising:
   a sample tube configured to contain therein a fluid;
   a fluidic element configured to aspirate a sample fluid from the fluid contained within the sample tube, the fluidic element coupled to a transfer arm movable to access the sample tube; and
   a heater in a position accessible by the fluidic element, the heater comprising:
   an induction coil sized and configured to allow for the fluidic element to be placed therein;

induction circuitry coupled to the induction coil and configured to generate a current to pass through the induction coil, thereby creating a field within the induction coil that generates heat transferrable to the fluidic element placed therein;

a sensing coil sized and configured to allow for the fluidic element to be placed therein; and level-sensing circuitry coupled to the sensing coil and configured to impose a signal on the fluidic element when placed in the sensing coil and detect a change in the imposed signal, wherein the change in the imposed signal serves as an indication that the fluidic element is in contact with the fluid contained within the sample tube;

wherein heat is imparted to the sample fluid from the heat transferred to the fluidic element prior to aspiration, during aspiration, and following aspiration depending upon an order in which the fluidic element is placed within the induction coil and aspirates the sample fluid.

5. The system of claim 4, further comprising:

a sensor configured to detect a temperature of the fluidic element placed within the induction coil, the sensor coupled to at least one of the fluidic element and the heater.

6. The system of claim 4, further comprising:

a sensor coupled to a dispensing unit, the sensor configured to detect a temperature of a portion of the sample fluid dispensed from the fluidic element to the dispensing unit.

7. The system of claim 4, further comprising:

a washing unit configured to wash the fluidic element after dispensing the sample fluid, wherein the heater generates a high temperature heat transferrable to the fluidic element placed within the induction coil to eliminate carry-over on the fluidic element.

8. The system of claim 4, wherein the fluidic element is configured to move between the sample tube and the heater.

9. The system of claim 4, wherein the heater is attached to the fluidic element.

10. A method of heating fluidic elements and fluids in an in vitro diagnostics (IVD) environment, the method comprising:

providing a sample tube containing therein a fluid;

providing a fluidic element configured to aspirate a sample fluid from the fluid contained within the sample tube and configured to fit within an induction coil of a heater and a sensing coil, the fluidic element coupled to a transfer arm movable to access the sample tube;

applying, through induction circuitry coupled to the induction coil, a current to pass through the induction coil, thereby creating a field within the induction coil that generates heat transferrable to the fluidic element placed therein;

detecting by level-sensing circuitry coupled to the sensing coil that the fluidic element is in contact with the fluid contained within the sample tube, wherein the level-sensing circuitry is configured to impose a signal on the fluidic element and detect a change in the imposed signal, wherein the change in the imposed signal serves as an indication that the fluidic element is in contact with the fluid; and aspirating, by the fluidic element, the sample fluid from the sample tube, wherein heat is imparted to the sample fluid from the heat transferred to the fluidic element prior to aspiration, during aspiration, and following aspiration depending upon an order in which the fluidic element is placed within the induction coil and aspirates the sample fluid.

11. The method of claim 10, further comprising:

detecting, via a sensor coupled to at least one of the fluidic element and the heater, a temperature of the fluidic element placed within the induction coil.

12. The method of claim 10, further comprising:

detecting, via a sensor coupled to a dispensing unit, a temperature of a portion of the sample fluid dispensed from the fluidic element to the dispensing unit.

13. The method of claim 10, further comprising:

washing, via a washing unit, the fluidic element after dispensing the sample fluid; and inserting the fluidic element into the induction coil of the heater, wherein the heater generates a high temperature heat transferrable to the fluidic element placed within the induction coil to eliminate carry-over on the fluidic element.

14. The method of claim 10, further comprising:

prior to aspirating, by the fluidic element, the sample fluid from the sample tube, removing the fluidic element from the induction coil of the heater.

15. The method of claim 10, wherein the heater is attached to the fluidic element.

* * * * *